(12) United States Patent
Dahm et al.

(10) Patent No.: US 9,622,762 B2
(45) Date of Patent: Apr. 18, 2017

(54) CATHETER DEVICES FOR CROSSING AND TREATING AN OCCLUSION

(71) Applicant: XableCath Inc., Salt Lake City, UT (US)

(72) Inventors: Johannes B. Dahm, Göttingen (DE); Bart M. E. Segers, Antwerp (BE)

(73) Assignee: XableCath Inc., Salt Lake City, UT (US)

( * ) Notice: Subject to any disclaimer, the term of this patent is extended or adjusted under 35 U.S.C. 154(b) by 0 days.

(21) Appl. No.: 14/682,963

(22) Filed: Apr. 9, 2015

(65) Prior Publication Data

US 2015/0209066 A1    Jul. 30, 2015

Related U.S. Application Data

(63) Continuation of application No. PCT/US2014/056162, filed on Sep. 17, 2014.
(Continued)

(51) Int. Cl.
*A61B 17/22* (2006.01)
*A61B 17/3207* (2006.01)
(Continued)

(52) U.S. Cl.
CPC .......... *A61B 17/22* (2013.01); *A61B 17/3207* (2013.01); *A61B 17/320725* (2013.01); *A61B 17/320758* (2013.01); *A61B 17/3439* (2013.01); *A61M 25/0043* (2013.01); *A61M 25/0136* (2013.01); *A61M 25/104* (2013.01); *A61B 2017/22001* (2013.01); *A61B 2017/22002* (2013.01); *A61B 2017/22038* (2013.01); *A61B 2017/22047* (2013.01); *A61B 2017/22051* (2013.01); *A61B 2017/22079* (2013.01); *A61B 2017/22094* (2013.01); *A61B 2017/320004* (2013.01); *A61B 2017/320044* (2013.01);
(Continued)

(58) Field of Classification Search
CPC .......... A61B 17/3207; A61B 17/32075; A61B 17/320758; A61B 17/320766; A61B 17/320775; A61B 17/320783; A61B 17/320791
USPC ........................................................ 606/159
See application file for complete search history.

(56) References Cited

U.S. PATENT DOCUMENTS 3,448,741 A    6/1969    Dennis et al.
4,471,777 A    9/1984    McCorkle, Jr.
(Continued)

OTHER PUBLICATIONS

Avinger, "Wildcat,, Kittycat, Kittycat 2—Designed for CTOs".
(Continued)

*Primary Examiner* — Tuan V Nguyen
(74) *Attorney, Agent, or Firm* — Knobbe Martens Olson & Bear LLP

(57) ABSTRACT

A device and method for treating a patient with total or near total occlusion is provided. The device can be positioned in a blood vessel at a treatment site. An occlusion at the treatment site is enlarged by a catheter. The catheter can be advanced over a guidewire into the occlusion. One or more of [a] compression or torsion applied to the guidewire or [b] compression or torsion applied to the catheter body expands or creates a path through the occlusion. The expansions or creation of the access path can be by cutting or abrading the occlusion or by a shoe-horn effect.

18 Claims, 15 Drawing Sheets

Related U.S. Application Data

(60) Provisional application No. 61/879,384, filed on Sep. 18, 2013.

(51) Int. Cl.
*A61B 17/34* (2006.01)
*A61M 25/00* (2006.01)
*A61M 25/01* (2006.01)
*A61M 25/10* (2013.01)
*A61B 17/32* (2006.01)

(52) U.S. Cl.
CPC ............ *A61B 2017/320716* (2013.01); *A61B 2017/320775* (2013.01); *A61B 2217/007* (2013.01)

(56) References Cited

U.S. PATENT DOCUMENTS

| | | | |
|---|---|---|---|
| 4,576,162 A | 3/1986 | McCorkle | |
| 4,582,056 A | 4/1986 | McCorkle, Jr. | |
| 4,732,154 A | 3/1988 | Shiber | |
| 4,754,755 A | 7/1988 | Husted | |
| 4,842,579 A | 6/1989 | Shiber | |
| 4,846,174 A | 7/1989 | Willard et al. | |
| 4,883,458 A | 11/1989 | Shiber | |
| 4,898,575 A | 2/1990 | Fischell et al. | |
| 4,923,462 A | 5/1990 | Stevens | |
| 4,957,482 A | 9/1990 | Shiber | |
| 4,979,939 A | 12/1990 | Shiber | |
| 5,041,082 A | 8/1991 | Shiber | |
| 5,047,040 A | 9/1991 | Simpson et al. | |
| 5,078,723 A | 1/1992 | Dance et al. | |
| 5,135,531 A | 8/1992 | Shiber | |
| 5,192,268 A | 3/1993 | Shiber | |
| 5,306,244 A | 4/1994 | Shiiber | |
| 5,334,211 A | 8/1994 | Shiber | |
| 5,419,774 A | 5/1995 | Willard et al. | |
| 5,443,443 A | 8/1995 | Shiber | |
| 5,512,044 A | 4/1996 | Duer | |
| 5,620,451 A | 4/1997 | Rosborough | |
| 5,632,754 A * | 5/1997 | Farley et al. | 606/159 |
| 5,651,781 A | 7/1997 | Grace | |
| 5,779,715 A | 7/1998 | Tu | |
| 5,782,847 A | 7/1998 | Plaia et al. | |
| 5,843,103 A | 12/1998 | Wulfman | |
| 5,865,844 A | 2/1999 | Plaia et al. | |
| 5,934,284 A | 8/1999 | Plaia et al. | |
| 5,980,515 A | 11/1999 | Tu | |
| 6,033,402 A | 3/2000 | Tu et al. | |
| 6,143,009 A | 11/2000 | Shiber | |
| 6,152,938 A | 11/2000 | Curry | |
| 6,167,315 A | 12/2000 | Coe et al. | |
| 6,183,469 B1 * | 2/2001 | Thapliyal et al. | 606/41 |
| 6,241,692 B1 | 6/2001 | Tu et al. | |
| 6,258,109 B1 * | 7/2001 | Barry | A61B 17/320758 600/585 |
| 6,440,148 B1 | 8/2002 | Shiber | |
| 6,763,270 B1 | 7/2004 | Gomperz et al. | |
| 6,772,014 B2 | 8/2004 | Coe et al. | |
| 6,818,002 B2 | 11/2004 | Shiber | |
| 6,824,550 B1 | 11/2004 | Noriega et al. | |
| 7,104,966 B2 | 9/2006 | Shiber | |
| 7,335,216 B2 | 2/2008 | Bender et al. | |
| 7,635,340 B2 | 12/2009 | Vetter et al. | |
| 8,021,330 B2 | 9/2011 | McAndrew | |
| 8,062,316 B2 | 11/2011 | Patel et al. | |
| 8,241,315 B2 | 8/2012 | Jenson et al. | |
| 8,361,097 B2 | 1/2013 | Patel et al. | |
| 8,377,084 B1 | 2/2013 | King, III et al. | |
| 8,435,228 B2 | 5/2013 | Wulfman et al. | |
| 8,439,937 B2 | 5/2013 | Montague et al. | |
| 8,480,696 B2 | 7/2013 | Clague et al. | |
| 8,696,695 B2 | 4/2014 | Patel et al. | |
| 8,702,679 B2 | 4/2014 | Deckman et al. | |
| 8,795,306 B2 | 8/2014 | Smith et al. | |
| 9,033,996 B1 * | 5/2015 | West | 606/129 |
| 2003/0125757 A1 * | 7/2003 | Patel et al. | 606/159 |
| 2003/0216761 A1 | 11/2003 | Shiber | |
| 2005/0021002 A1 | 1/2005 | Deckman et al. | |
| 2005/0137622 A1 | 6/2005 | Griffin | |
| 2007/0032808 A1 | 2/2007 | Anwar et al. | |
| 2007/0185510 A1 | 8/2007 | Tran | |
| 2007/0250096 A1 | 10/2007 | Yamane et al. | |
| 2007/0276419 A1 | 11/2007 | Rosenthal | |
| 2008/0039883 A1 | 2/2008 | Nohilly | |
| 2008/0045986 A1 * | 2/2008 | To | A61B 17/320758 606/159 |
| 2008/0058722 A1 | 3/2008 | Von Oepen et al. | |
| 2008/0071341 A1 * | 3/2008 | Goode et al. | 607/122 |
| 2008/0071342 A1 | 3/2008 | Goode et al. | |
| 2008/0114390 A1 | 5/2008 | Guinan | |
| 2008/0154296 A1 | 6/2008 | Taylor et al. | |
| 2008/0161841 A1 | 7/2008 | Clague et al. | |
| 2008/0319462 A1 | 12/2008 | Montague et al. | |
| 2009/0018566 A1 | 1/2009 | Escudero et al. | |
| 2009/0018567 A1 | 1/2009 | Escudero et al. | |
| 2009/0156983 A1 | 6/2009 | Bonnette et al. | |
| 2009/0264907 A1 | 10/2009 | Vrba et al. | |
| 2009/0270890 A1 | 10/2009 | Robinson et al. | |
| 2010/0082051 A1 | 4/2010 | Thorpe et al. | |
| 2010/0114136 A1 | 5/2010 | Clague et al. | |
| 2010/0274270 A1 | 10/2010 | Patel et al. | |
| 2011/0034937 A1 | 2/2011 | Mustapha et al. | |
| 2011/0054503 A1 | 3/2011 | Rizk et al. | |
| 2011/0152904 A1 | 6/2011 | Clague et al. | |
| 2011/0152906 A1 | 6/2011 | Escudero et al. | |
| 2011/0178543 A1 * | 7/2011 | Chin | A61B 17/50 606/190 |
| 2011/0218528 A1 | 9/2011 | Ogata et al. | |
| 2011/0319905 A1 | 12/2011 | Palme et al. | |
| 2012/0004596 A1 | 1/2012 | Thomas | |
| 2012/0041307 A1 | 2/2012 | Patel et al. | |
| 2012/0101510 A1 * | 4/2012 | Lenker | A61B 17/12118 606/159 |
| 2012/0109171 A1 | 5/2012 | Zeroni et al. | |
| 2012/0158039 A1 * | 6/2012 | Angel et al. | 606/200 |
| 2012/0197193 A1 | 8/2012 | Krolik et al. | |
| 2012/0203163 A1 | 8/2012 | Thomas | |
| 2012/0323252 A1 * | 12/2012 | Booker | A61B 17/320016 606/129 |
| 2013/0035750 A1 | 2/2013 | Rizk et al. | |
| 2013/0138128 A1 | 5/2013 | Patel et al. | |
| 2013/0289392 A1 | 10/2013 | Patel et al. | |
| 2014/0005699 A1 | 1/2014 | Bonnette et al. | |
| 2014/0214059 A1 | 7/2014 | Andersen | |
| 2014/0222048 A1 | 8/2014 | Ladd | |
| 2014/0243734 A1 | 8/2014 | Eubanks et al. | |
| 2014/0277004 A1 | 9/2014 | Thatipelli | |
| 2014/0277009 A1 | 9/2014 | Thatipelli | |
| 2015/0209057 A1 | 7/2015 | Dahm et al. | |
| 2015/0209064 A1 | 7/2015 | Dahm et al. | |
| 2015/0209065 A1 | 7/2015 | Dahm et al. | |

OTHER PUBLICATIONS

Boston Scientific, http://www.bostonscientific.com/en-EU/products/cto-systems/truepath-cto-device.html, "TruePath™ Chronic Total Occulsion Device (CTO) Device", 2015.
Boston Scientific, "OffRoad™ Re-entry Catheter System", 2014.
Cook Medical, "CXI Support Catheter", 2009.
Cordis® a Johnson & Johnson Company, "Endovascular—Chronic Total Occlusion (CTO) Technologies", Dec. 2008.
COVIDIAN, "Viance™ Crossing Catheter; Enteer™ Re-entry System—Advanced design for CTO treatment", 2012.
CTO Product Portfolio, "Crosser® Recanalization System", BARD Peripheral Vascular, 2013.
Ev3, "TrailBlazer Procedural Support", 2010.
International Search Report and Written Opininon issued in PCT Application No. PCT/US2014/056162, dated Mar. 19, 2015, in 13 pages.

(56) References Cited

OTHER PUBLICATIONS

ReFlow Medical, "Wingman", Screenshot of http://www.reflowmedical.com/wingman/downloaded Apr. 9, 2015.
Volcano Precision Guided Therapy, "Pioneer+Plus—Intravascular Ultrasound Guided Re-Entry Catheter".
U.S. Appl. No. 14/682,825, Support Catheters for Use in Crossing and Treating an Occlusion, filed Apr. 9, 2015.
U.S. Appl. No. 14/682,897, Methods for Crossing and Treating an Occlusion, filed Apr. 9, 2015.
U.S. Appl. No. 14/682,821, Systems for Use in Crossing and Treating an Occlusion, filed Apr. 9, 2015.
International Preliminary Report on Patentability issued in PCT Application No. PCT/US2014/056162, dated Mar. 22, 2016, in 7 pages.
Antman et al., "The TIMI Risk Score for Unstable Angina/Non-ST Elevation MI: A Method for Prognostication and Therapeutic Decision Making FREE", JAMA., 2000, vol. 284, No. 7, pp. 835-842.
Fang et al., "Can a Penetration Catheter (Tornus) Substitute Traditional Rotational Atherectomy for Recanalizing Chronic Total Occlusions?", Int Heart J, May 2000, vol. 51, No. 3, pp. 147-152.
Fernandez et al., "Laser atherectomy for stent underexpansion", EuroIntervention, 2011, vol. 7, pp. 400-407.
Gronenschild et al., "CAASI. II: A second generation system for off-line and on-line quantitative coronary angiography", Cathet. Cardiovasc. Diagn., Sep. 1994, vol. 33, No. 1, pp. 61-75.
Haase et al., "Experimental validation of geometric and densitometric coronary measurements on the new generation Cardiovascular Angiography Analysis System (CAAS II)", Cathet. Cardiovasc. Diagn., Oct. 1993, vol. 30, No. 2, pp. 104-114.
Hirokami et al., "Anchoring technique to improve guiding catheter support in coronary angioplasty of chronic total occlusions", Cathet. Cardiovasc. Intervent., Mar. 2006, vol. 67, No. 3, pp. 366-371.
Mahmood et al., "Applications of the Distal Anchoring Technique in Coronary and Peripheral Interventions", J Invasive Cardiol, Jul. 2011, Vo.. 23, No. 7.
Michael et al., "Subintimal Distal Anchor Technique for Balloon-Uncrossable Chroinc Total Occlusions", J Invasive Cardiol, Oct. 2013, vol. 25, No. 10.
Pagnotta et al., "Rotational atherectomy in resistant chronic total occlusions", Cathet. Cardiovasc. Intervent., Sep. 1, 2010, vol. 76, No. 3, pp. 366-371.

\* cited by examiner

CATHETER DEVICES FOR CROSSING AND TREATING AN OCCLUSION

BACKGROUND OF THE INVENTION

Field of the Invention

This application is directed to systems and methods for treating occlusions, including crossing narrow passages of lumen segments or total occlusions.

Description of the Related Art

A variety of techniques exist to de-bulk occluded vessel segments. While these techniques have met varying degrees of success, not all patients are successfully treated in this manner. Some patients with peripheral occlusions are left with few options other than amputation of the limb fed by the occluded artery. Such drastic techniques are obviously not available to patients with extensive occlusion of coronary and other critical arteries.

There are a number of products on the market that are designed specifically for crossing CTOs and these can be categorized as either intraluminal, subintimal or re-entry devices. Intraluminal crossing in theory may reduce the dissection plane of a long occlusive lesion, protect collaterals and keep treatment options open. Subintimal crossing may extend "re-entry" beyond the occluded segment, putting collaterals at risk and limiting treatment options. It may also increase the rates of complications such as perforation and dissection and extend procedure time with resultant increased radiation and contrast exposure. Also below the knee, once a wire has crossed into the adventitia it can be extremely difficult to re-enter the true lumen.

Certain catheter systems have been developed to cross occlusions in an intraluminal manner. However, these catheter systems have problems. For instance three or more coaxially placed catheter bodies can work in a system to cross a lesion. An inner solid guidewire member can be provided within an outer sheath. An intervening rotatable layer can be advanced over the guidewire from within the outer sheath to gouge or chisel the occlusion mass slowly away. One problem with this structure is that with three or more components, two operators may be needed to handle components of the device.

Also, with more calcified lesions typical catheter bodies are not well suited to provide access. Generally, catheter bodies are of reduced stiffness toward the distal end thereof to minimize potential for trauma to healthy vascular tissues. However, in order operate on highly calcified lesions, the tip of the device should have greater stiffness.

Another problem with conventional techniques is (i.e., atherectomy-devices) is that debris of atheroma may embolize and may lead to distal embolization including no-reflow phenomenon. In addition, for these devices greater arterial access sheaths are mandatory, which lead to more vascular complications in this normally very ill patients.

SUMMARY OF THE INVENTION

For these reasons, there exists a need for a flexible, low-profile occlusion crossing catheter that is able to cross a region of vessel stenosis and establish a passageway sufficient to accommodate a balloon catheter or other interventional device. The crossing catheter can be a delivery catheter in some implementations.

In one embodiment, a system is provided for creating an enlarged passage across an occlusion within a blood vessel or cylindrical body cavity. The system includes a guidewire and a catheter device. The guidewire has free distal and proximal ends. The guidewire is configured to be advanced relative to an occlusion and has an outer diameter. The catheter device has a flexible body, an implement, and a handle. The elongate body extends between a proximal end and a distal end. The elongate body having a lumen extending therethrough with an inner diameter larger than the outer diameter of the guidewire. The implement has a distal face, a side surface and a proximal end engaged with, e.g., disposed over, the distal end of the elongate body. The distal end of the implement is configured to act upon a portion of the occlusion. The handle is disposed at the proximal end of the elongate body. The system is configured such that distal pressure on the handle urges the implement distally to firmly engage the occlusion. The lumen provides lateral support to the guidewire in some techniques. In other techniques, the catheter itself primarily or solely acts upon the occlusion to enhance a passage therethrough. The system is configured such that rotation of the handle causes the elongate body and the implement to be rotated to enlarge the passage.

In another embodiment, a catheter for providing access across an occlusion is provided. The catheter has an elongate flexible body and an occlusion implement. The occlusion implement is a device used to clear a path through an occlusion as discussed herein. The elongate flexible body extends between a proximal end and a distal end. The occlusion implement has a rigid distal face and a cylindrical body extending proximally therefrom. The cylindrical body is configured to be juxtaposed relative to a distal portion of the elongate flexible body over an interface. The catheter body is configured to be advanced within the vasculature to an occlusion. In one embodiment or technique, the catheter body is configured to be advanced over a guidewire to the occlusion. In one embodiment or technique, the catheter body is configured to be advanced within the vasculature with an outer surface thereof exposed to the vasculature. In another embodiment or technique, the catheter body is configured to be advanced within a sheath within the vasculature. In such embodiments or techniques, the outer surface thereof, e.g., including at least the occlusion clearing implement, is exposed adjacent to the occlusion. In another embodiment or techniques, the catheter body is configured to be advanced unguided to an occlusion and to enhance access across an occlusion without the presence of a guidewire.

Preferably the occlusion implement has sufficient crush resistance to enable the energy or motion applied to the catheter to be used to enhance the access across the occlusion rather than to be used in deforming the occlusion implement. A distal tip or occlusion engaging portion should be more crush resistant than a more proximal structure, e.g., than the catheter body. The occlusion implement can be configured to retain a minimum transverse dimension of at least about 90% of its diameter upon application of a crush force of about 15 psi whereby deformation of an inner passage thereof is minimal during interaction with an occlusion. The occlusion implement can be configured to retain a minimum transverse dimension of at least about 90% of its diameter upon application of a crush force of about 25 psi whereby deformation of an inner passage thereof is minimal during interaction with an occlusion.

In some variations, the occlusion implement can be configured to retain a minimum transverse dimension, e.g., of at least about 90% of its original or at rest diameter, upon application of a crush force of about 3 Newton, in some cases as much as 5 Newton, in some cases up to and exceeding 7 Newton, and in some cases 10 Newton or more.

In some embodiments, the occlusion implement has a hoop strength greater than 15 psi or in some cases as much as 25 psi to minimize out or round of the implement so that the implement will not bind upon a guidewire or guide catheter during use.

The catheter can provide other useful functions or can have other useful features. For example, the catheter can be configured to be a conduit for contrast injection in some methods. The injection of contrast can be used to illuminate, e.g., to provide information about the operational state of the catheter, e.g., indicate if it is blocked by abraded matter.

In some embodiments, the catheter has variable stiffness, for example has high stiffness at or near its distal end to enhanced occlusion abrading, reducing or eliminating effect. Proximal of the distal end, the flexibility of the catheter can be greater.

In some techniques, clearing the occlusion can involve removing one or more guidewires and exchanging one guidewire for another guidewire. For example, a flexible wire could be exchanged for a stiff wire or a stiff wire for a flexible wire. It is preferred that such maneuvers do not disturb the position of the distal end of the catheter significantly. Thus, a lubricious coating or material can be provided along the surface forming the guidewire lumen of the catheter. Also, the other surface can comprise or be coated with a lubricious material to reduce the force needed to advance the catheter exposed within the vasculature or within a guide catheter.

In various embodiments below, the shape of cutting features, e.g., teeth, on the distal end of the catheter can be configured to address certain types of occlusive matter. Harder occlusive matter may be more efficiently cleared using teeth or similar structures that deliver a focused force. Less hard occlusive matter may be more efficiently cleared using less aggressive teeth or similar structures, which can act more like a shoe-horn to scoop such material from the vessel lumen.

In some embodiments, an approach for addressing the tip or occlusion clearing implement filling with material is provided. The approach may involve exchanging one filled catheter for a clear catheter. In this technique, a catheter is advanced, is filled, and is then removed with a core of material captured therein. Then a second catheter is advanced, filled and removed. This procedure is continued until a path through the occlusions is sufficiently large. Because each removed core may enlarge the bore of or lengthen the passable portion of the occlusions somewhat, second and subsequent catheters can be longer or can have larger internal lumens and/or cutting implements. In other approaches, an aspiration lumen is provided through the catheter. The aspiration lumen can be the same lumen as the guidewire lumen, e.g., a large central lumen. In other embodiments, separate aspiration lumens can be provided in the wall of the catheter. In this context, aspiration can include removing by negative pressure dislodged portions of the occlusion entirely from the patient's body and from the catheter. Aspiration can also include just taking the dislodged portions up into a passage in the catheter but not necessarily fully out of the patient's body and out of the catheter while the catheter is in the body.

In some embodiments, the tip of the catheter is flat, e.g., is perpendicular to the longitudinal axis of the lumen of the catheter. An advantage of this configuration is that it is more deliverable within the patient, e.g., in an exposed approach without a sleeve covering the tip. Angled tips may be used, and when used may be delivered in a protective sheath in some embodiments or in some techniques involving tortuous vasculature (e.g., in coronary vasculature or in neuro vasculature). Angled tips may be delivered in an exposed state in techniques involving straight or non-tortuous vasculature (e.g., in peripheral vasculature).

An advantage of the catheter is that the distal tip will generally include or be formed of a material that is highly opaque under X-ray. Thus, as the device is being delivered the clinician can easily see the tip, which can help with its safe delivery to the treatment site, even without the need to inject a contrast medium and, in some techniques, even without a sheath or guidewire. Safety of delivery can also be provided by maintaining the outer diameter of the catheter to a fraction of the unoccluded vessel size. For example, the catheter can be maintained at about one-quarter the size or in some cases as small as one-eighth the size of the vessel diameter. In such embodiments, the cutting tip preferably has a length about equal to the vessel diameter. This aspect ratio enables the cutting or abrading portion of the catheter to stay centered in and aligned with the longitudinal axis of the vessel. These configurations are particularly suited for non-tortuous, e.g., straight, vessels as are found in the legs and other peripheral vasculature.

In another embodiment, a method of treating a patient with total or near total occlusion is provided. In the method a blood vessel is accessed. The access can be by any catheter technique. A guidewire is advanced into the patient to a treatment site. The treatment site has an occlusion that is desired to be cleared or enlarged, for example a total or near total occlusion. A catheter is advanced over the guidewire into apposition with a proximal portion of the occlusion. The catheter has a lumen therethrough and a distal occlusion engaging portion, e.g., an anchor face, at a distal end thereof. The anchor face can be in the form of high friction or sharp features to enable the clinician to selectively prevent rotation of a catheter. One or more of [a] compression force or torsion to the guidewire or [b] compression force or torsion is applied to the catheter body to expand or create an access path through the occlusion. An anchor face or other distal occlusion engaging portions can provide stability, like a climber's crampon, to the catheter while a wire is being advanced or rotated therein to help provide access across the occlusion. The expansions of the access path can be by cutting or abrading the occlusion. In some cases, the expansion can be provided or enhanced by a shoe-horn effect.

In another embodiment, a catheter is provided for providing access across an occlusion. The catheter includes an elongate catheter assembly, a lesion clearing implement, and an interface. The elongate catheter assembly extends between a proximal end and a distal end. The lesion clearing implement has a ring structure. The interface is disposed between the ring structure and the elongate catheter assembly. The interface provides a protrusion disposed on one of [a] the elongate catheter assembly and the ring structure and [b] a recess disposed on the other of the elongate catheter assembly and the ring structure. The interface is at least partially in a radial direction such that an axial load can be transmitted across the interface.

In some embodiments, the interface is provided such that a protrusion and recess overlap in the axial direction.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE PREFERRED EMBODIMENT

Each and every feature described herein, and each and every combination of two or more of such features, is included within the scope of the present invention provided that the features included in such a combination are not mutually inconsistent.

Embodiments of the present invention are generally directed to catheter systems for crossing vascular stenosis, such as near total occlusions, components thereof, and methods use of such systems and components.

As used herein, the term "near total occlusion" refers to regions of vascular stenosis that reduce the cross-sectional area of the vessel lumen by >80%, in particular, by >90%, and in some cases by more than 95%. The term "total occlusion" means the entire vessel lumen is fully occupied by atheroma or other occlusive material preventing blood flow through the passage of the lumen.

As used herein, the term "substantially", when used in reference to a linear dimension (e.g., length, width, thickness, distance, etc.) means within plus or minus one percent (1%) of the value of the referenced linear dimension.

Figure 1:
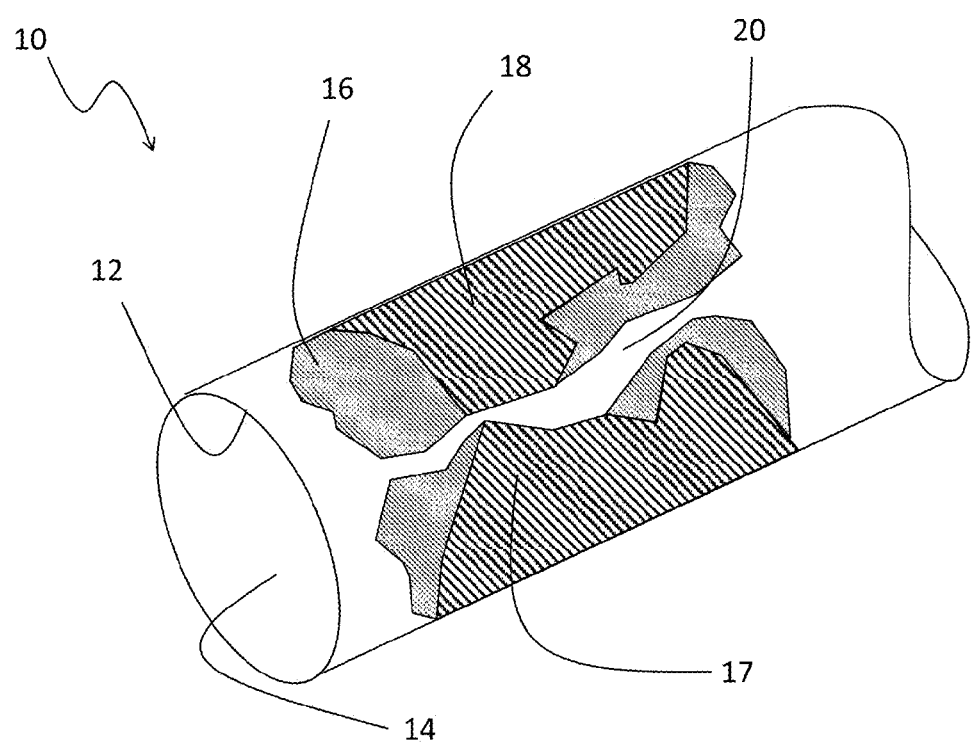
FIG. 1 illustrates schematically a near total occlusion.

FIG. 1 is a cartoon representation of a near total occlusion of a blood vessel formed by a lesion 17. The blood vessel 10 has an interior surface 12, which defines a lumen 14. In atherosclerosis, lipid and fibro muscular material accumulate in the vessel wall, forming a lesion that bulges into and occupies or occludes at least a portion of the lumen 14. Advanced-stage atherosclerotic lesions often include regions of soft plaque 16 and regions of atheroma 18. In some cases, the atheroma 18 may be calcified making access by interventional techniques difficult or impossible.

When the atheroma 18 intrudes into the lumen 14, a stenosis 20 is formed that can greatly reduce blood flow through the vessel. Angioplasty is one technique for treating a stenosis 20. In balloon angioplasty, a deflated balloon is mounted on an endovascular catheter, and the catheter is pushed along the vessel 10 until the deflated balloon occupies at least a portion of the stenosis 20. Once the deflated balloon is positioned within the stenosis 20, the balloon is inflated, pushing the atheroma 18 back toward the vessel wall and enlarging the lumen 14 within the region of stenosis 20. In some cases, an expandable stent is used to restore the lumen 14 within the region of stenosis 20.

In many cases, a guidewire is pushed ahead of the endovascular catheter to aid catheter travel through the blood vessel. The guidewire is thin and has a smaller profile than the catheter. Often, the catheter has a central lumen that accommodates the guidewire, and the catheter rides along the guidewire. This configuration of catheter is referred to as an "over-the-wire" catheter.

In some cases, the stenosis 20 is so narrow that the balloon catheter is unable to follow the guidewire through the stenosis. Rather, the balloon catheter can get hung-up or blocked at the proximal or distal end (depending on the direction of approach) of the stenosis 20. In such a case, angioplasty is precluded because it is not possible to position a deflated balloon within the stenosis 20. In some cases, the atheroma 18 forms a calcified plug that precludes passage of the guidewire through the stenosis 20.

Figure 1A:
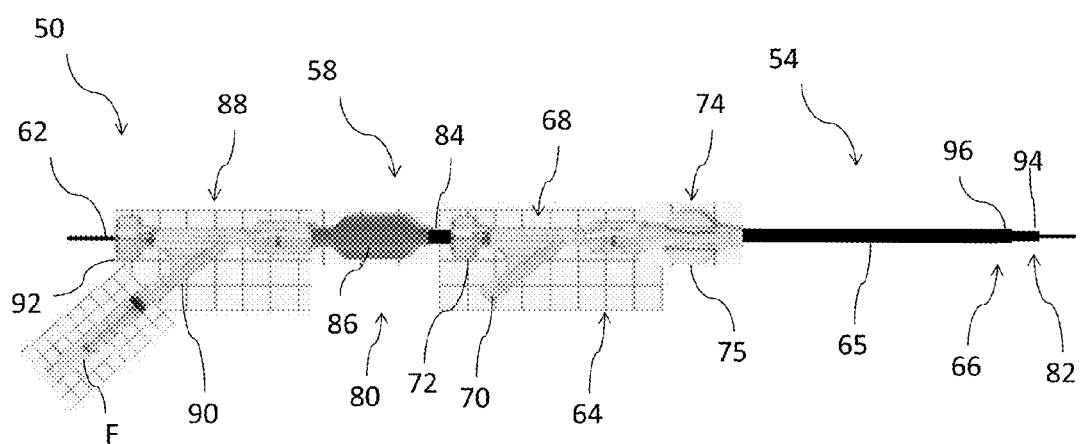
FIG. 1A illustrates a system the can be used to provide access across an occlusion for therapy devices to enhance treatment of an occlusion.

FIG. 1A illustrates an occlusion crossing system 50 that can be used to improve a clinician's ability to pass a balloon catheter or other therapy device across a blockage formed by the lesion 17. The occlusion crossing system 50 includes a sheath 54 and a catheter device 58. The catheter device 58 is provided for clearing a passage through the lesion 17 to enlarge the access therethrough, which may involve cutting the occlusion. For this reason, in some passages the catheter device 58 is referred to as a cutting catheter. The sheath 54 can be used to enclose and/or guide the catheter device 58 between a vascular access site and an occlusion. The sheath 54 thus provides protection for the un-occluded vessel(s) through which the catheter device 58 is delivered. The occlusion crossing system 50 can also include a guidewire 62 to help access or cross an occlusion.

The guidewire 62 can take any suitable form. It can be a long slender wire with no lateral protuberances or it can have one or more lateral extensions. For example a plurality of barriers or shoulders can be provided along a distal length of the guidewire 62 to engage and retain portions of the lesion 17. The guidewire 62 can have an anchor, such as a helical structure adapted to be advanced rotationally into the lesion to engage and hold it. These are examples of structures that can positively engage and hold the lesion 17. When so engaged, these structures can provide a counter traction for holding the position of the lesion while catheter device 58 (or variant herein) is advanced into the lesion to enhance access across the lesion. Examples of barriers and anchor are discussed in U.S. Pat. No. 5,443,443 and U.S. Pat. No. 5,047,040, which are hereby incorporated by reference herein in their entirety.

The sheath 54 comprises a proximal end 64, a distal end 66, and a lumen extending through an elongate body 65 disposed between the ends 64, 66. The lumen is sized to receive the catheter device 58 as discussed further below. The proximal end 64 of the sheath 54 is preferably configured to be coupled with other devices. For example, a branched access port 68 can be provided at the proximal end 64. A first branch 70 can be provided to couple with a fluid source. A second branch 72 can be aligned with the lumen of the sheath 54 to provide in-line access to the lumen of the sheath 54. One or both of the branches 70, 72 can have a valve structure to limit, minimize or eliminate blood loss. A tuohy-borst attachment can be provided on one or both of the branches 70, 72. In one embodiment, the proximal end 64 includes a modular coupling 74 that enables the branched access port 68 to be decoupled from the elongate body 65 if access via the branches is not required or for certain phases of procedures where the branches are not needed and might be in the way if not removed from the procedure zone. The coupling 74 can include torque structures 75 on opposite sides thereof.

The catheter device 58 is configured to be advanced to the occlusion 20 to provide a therapy as discussed herein. The catheter device 58 comprises a proximal end 80, a distal end 82, and a lumen extending through an elongate body 84 disposed between the ends 80, 82. The lumen is sized to provide access for a balloon catheter or other therapy device, for fluid to be injected or withdrawn, and/or for material of the occlusion 20 to be lodged. The elongate body 84 has sufficient rigidity for deliverability and for providing cutting or segmenting action at the occlusion 20. For example the body 84 can be configured to provide 1:1 torque. As discussed below, braids and coils are contemplated as structures providing pushability and flexibility for various applications, including peripheral, coronary and neuro-vascular applications.

The elongate body 84 has a length sufficient to reach a treatment site such as a peripheral, coronary, or neuro-vascular treatment site. For example, for ipsa-lateral treatment, the elongate body 84 can be between about 40 and about 100 cm, e.g., about 80 cm. For a treatment in the iliac artery, the elongate body 84 can be about 60 cm. For a treatment in the superficial femoral artery (SFA), the elongate body 84 can be between about 140 and 160 cm. For a treatment in the coronary arteries, the elongate body 84 can be between about 110 cm and about 140 cm. For neurovascular applications the elongate body 84 can be between about 130 cm and about 180 cm, e.g., about 150 cm. The sheath 54 can be about 10 cm to about 20 cm shorter than the catheter device 58. The elongate body 65 can be 10-20 cm shorter than the elongate body 84. More generally, the sheath 54 or elongate body 65 can be shorter than the catheter device 58 or elongate body 84 by an amount sufficient to provide a working length.

FIG. 1A shows that the lumen in the body 84 can receive the guidewire 62 in certain embodiments and for certain techniques. The proximal end 80 of the catheter device 58 is preferably has a handle 86 that is used to actuate the catheter 58. The handle 86 is configured to transmit a torque. The proximal end 80 can also include a branched access port 88 or other access device. A first branch 90 can be provided to couple with a fluid source F. A second branch 92 can be aligned with the lumen of the cutting catheter 58 to provide in-line access to the lumen in the body 84. One or both of the branches 90, 92 can have a valve structure to limit, minimize or eliminate blood loss. A tuohy-borst attachment can be provided on one or both of the branches 90, 92. In one embodiment, the branched access port 88 can be detached from the handle 86 when access via the branches 90, 92 is not required or for certain phases of procedures where the branches are not needed and might be in the way if not removed from the procedure zone. In one technique, the branched access port 88 is left in place when torqueing the catheter 58 because the first branch 90 provides a higher torque than the handle 86 in an optional system and technique.

The distal ends 66, 82 can be configured to be incompressible and/or radiopaque. The distal end 82 can be configured to engage and disrupt the occlusion 20 to enhance access through the stenosis 20. The distal end 82 preferably is stiffer than the elongate body 84 at locations proximal of the distal end 82. The end 82 includes an occlusion clearing implement 94, which can be one or more teeth, a continuous but abrasive surface for removing matter, a concave scooping structure for separating volumes of the matter from the occlusion 17 or other structures discussed herein. As discussed further below, the implement 94 or the system 50 are configured to follow a directed path and not to cause vessel injury in regions not being treated. The implement 94 can be radiopaque to provide visualization of the cutting catheter 58 when disposed in the vasculature.

The sheath 54 is configured to slideably and rotatably receives the catheter device 58. The inner surface of elongate body 65 and/or the outer surface of elongate body 84 can be configured to ease a retracting or extending motion in an axial direction, e.g., along the longitudinal axis of the body 65 or the body 84. Either of these surfaces can have a lubricious coating, for example. In one embodiment, the inner surface of the body 84 includes an expanded polytetrafluoroethylene (ePTFE) or other similar liner. As a result, the end 82 of the cutting catheter 58 can be pulled back into the end 66 of the sheath 54 for delivery or pushed out from the end 66 for engagement with the occlusion 20. The end 66 is configured to minimize out-of-round conditions of the sheath 54. In particular, a support ring 96 of the body 65 can be made more rigid than portions of the elongate body proximal of the distal portion 96 such that the elongate body 84 can freely rotate within the body 65. For example the support ring 96 can include a metal or ceramic cylinder that has hoop strength preventing it from being deformed when urged against an occlusion. The rigidity of the support ring 96 provides the advantage that the distal end 66 will maintain its pre-delivery configuration or will be deformed only by an amount that would not restrict rotation of the body 84 and thereby the end 82. The support ring 96 can be made of a radiopaque material to enhance visibility of the sheath 94 and the system 50.

Figure 2:
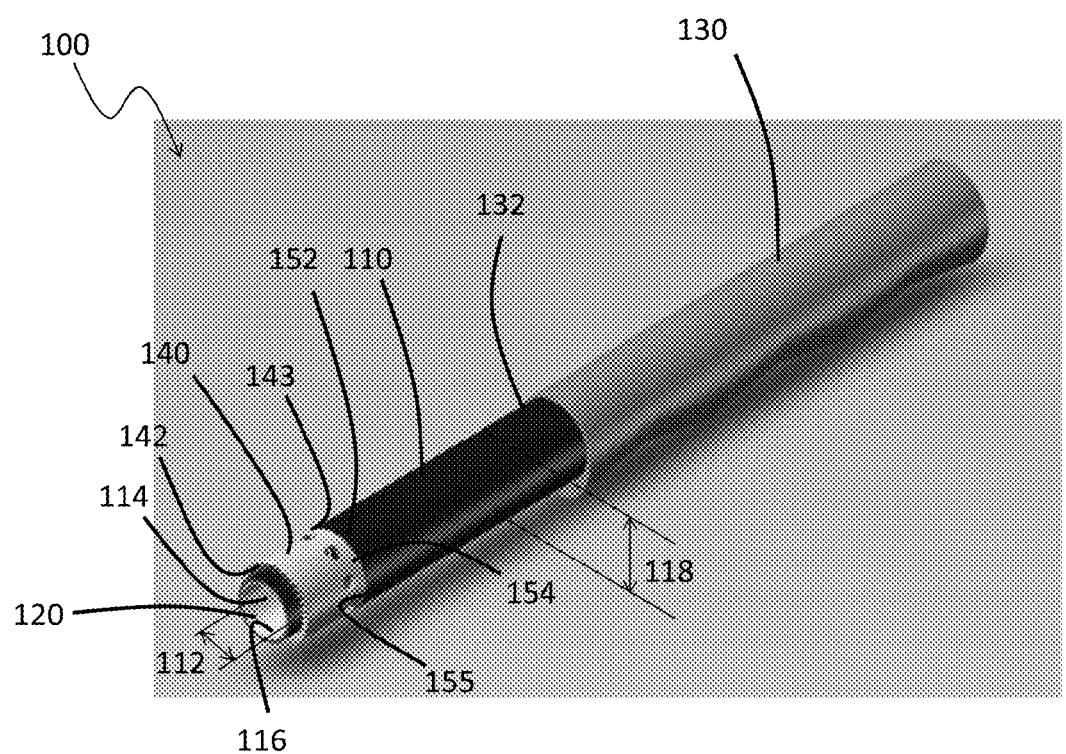
FIG. 2 is a perspective view of a first embodiment of a device that can be used in the system of FIG. 1A in providing access across an occlusion for therapy devices.

Methods of using the occlusion crossing system 50 or similar systems with any of the alternative components described herein are discussed below FIG. 2 depicts an embodiment of a clearing device 100. The clearing device 100 as or in combination with the catheter device 58 in the occlusion crossing system 50 discussed above. In the illustrated embodiment, the clearing device 100 has a handle 130 at a proximal end, a tip 140 at a distal end, and a flexible elongate body 110 that is coupled to the handle 130 and the tip 140.

In some embodiments, the elongate body 110 is hollow and cylindrical or substantially cylindrical, having an internal surface 116, a central lumen 114, an inner diameter 112, and an outer diameter 118. In several embodiments, the inner diameter 112 is about 0.94 mm to about 1.07 mm. In several embodiments, the outer diameter 118 is about 1.12 mm to about 1.37 mm. In some embodiments, the central lumen 114 is configured to accommodate a guidewire (not shown). In at least one embodiment, the inner diameter 112 is less than 10% larger than the outer diameter of a guidewire. In other embodiments, a smaller gap on a percentage basis may be provided. For example, some embodiments provide a less than 5% gap between the inner diameter thereof and an outer diameter of a guidewire (e.g., the guidewire 62 of FIG. 1A).

In other embodiments and techniques, the guidewire is used to track the clearing device 100 and specifically the tip 140 to the stenosis. Once in position, the guidewire could be withdrawn and the clearing device 100 can be used to enhance access across the occlusion. If the guidewire is in place the clearing device 100 system may rotate about the outer surface of the guidewire independently either exposed in the vessel or in the sheath 54. Thus, in some embodiments, the guidewire is not required to be in place or to rotate with the system for the device to function. In other embodiments and for certain applications, a guidewire may not be used even for delivery of the system. For example, if the vessel segment is straight there may not be a need for a guidewire. In such cases, the clearing device 100 preferably is configured to enhance access across an occlusion without support from a guidewire.

One feature that aids in guidance of the clearing device 100 whether guided by a wire or a guide catheter is the configuration of a rigid distal portion, for example of the tip 140. The tip 140 can be configured to minimize wandering within a blood vessel. In particular, blood is subject to varying pressures and certain peripheral blood vessels have a relatively high mobility. By making the length of the tip 140 greater than inner diameter 112 the distal portion of the clearing device 100 tends to remain generally straight in the vessel. In some embodiments, the length of the tip 140 is more than two times the diameter of the tip. In some embodiments, the length of the tip 140 is more than two and one-half times the diameter of the tip. In some embodiments, the length of the tip 140 is more than three times the diameter of the tip. The length of the tip 140 can be from 1-5 times the diameter of the tip in certain embodiments.

More generally, the clearing device 100 is not limited to natural body lumens or blood vessels. For example, another application for which the clearing device could be used is for salvaging occluded dialysis grafts. Such application may benefit from a lower profile clearing device, e.g., one having an outer diameter of bout 4-8 mm.

In some embodiments, a lining 120 covers at least a portion of the inner surface 116. In some embodiments, the lining 120 is made of a material that enhances the lubricity of the inner surface 116. In at least one embodiment, the lining 120 is made from ePTFE. The lining 120 or other lubricious structure or coating such as silicone or surface modification facilitates sliding of the elongate body 110 over a guidewire in a manner that reduces or minimizes forces that would tend to change the tracking force, the torque force, and the position of a the distal portion, such as a tip of the clearing device 100. As discussed below, in one mode the tip of the clearing device 100 is rotated about the guidewire to provide an abrading or gentle cutting action. Such action could be prevented if the distal portion, e.g., the tip becomes out of round due to such forces.

In several embodiments, the outer surface of the clearing device 100 is coated with a lubricious coating or structure to reduce friction with the vessel wall during tracking, torqueing, and crossing of the stenosis. Examples of such structures include a layer of Teflon, silicon, or a hydrophilic coating. A lubricious sleeve could be used, which sleeve can be moveable relative to, e.g., configured to be withdrawn from the clearing device 100.

Figure 6:
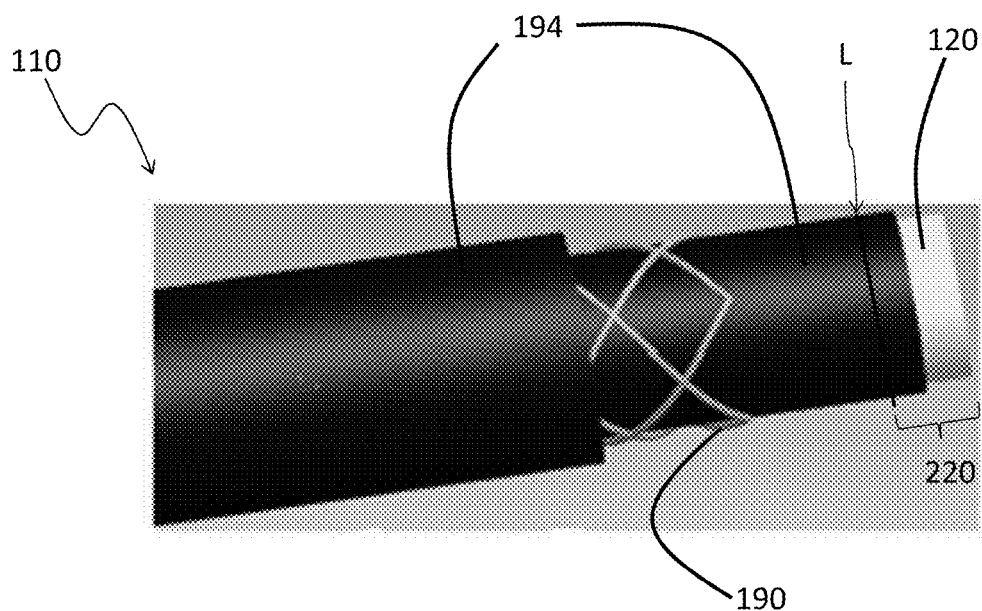
FIG. 6 is a cut-away view of a distal portion of a catheter body illustrating how the catheter body provides enhanced stiffness in a distal portion.

In several embodiments, the clearing device 100 has a tip 140 that is coupled to a distal end 152 of the elongate body 110. In some embodiments, a proximal end 154 of the tip 140 is disposed over the distal end 152 of the elongate body 110. In some embodiments, the distal end 152 of the elongate body 110 is disposed over the proximal end 154 of the tip 140. In at least one embodiment, the proximal end 154 of the tip 140 is coupled face-to-face with the distal end 152 of the elongate body 110 such that the tip 140 and the elongate body 110 share a similar outer diameter, with a proximal face 143 of the tip 140 forming an interface with a distal face 155 of the elongate body 110. In some cases, a transition between the proximal face 143 and a distal end of the elongate provide a joint without a step that could catch on external matter as the device 100 is being delivered. In several embodiments, the cutting tip is attached to the braided skeleton of the catheter body prior to coating the entire structure with an extruded polymer, after which the tip can be subsequently exposed. Other reinforced catheter designs tend to store energy in the reinforcement. The result is something like winding a spring rather than providing one-to-one rotation of the distal end upon rotation of the proximal end. In the catheters herein the braided skeleton is preferably formed to reduce storing energy in the catheter body and to maintain as close as possible one-to-one rotation to enhance the cutting work at the distal end for the rotation at the proximal end. FIG. 6 shows a mesh material 190 to which the tip could be welded or otherwise coupled, for example. In other embodiments, the cutting tip can be attached to the catheter with an adhesive. Variations provide multiple layers of adhesive and layers that can be applied or heat-shrunk over inner layers of the clearing device 10. In some cases, as described herein a recess and/or protrusion provide a strong mechanical interface alone or in combination with other attachment structures.

In several embodiments, the clearing device 100 has a handle 130 coupled to the proximal end 132 of the elongate body 110. In some embodiments, the handle 130 is configured to apply torque to the elongate body 110 as a user rotates the handle 130. In at least one embodiment, the clearing device 100 is configured so that the handle 130 applies an approximately a 1:1 torque ratio to the elongate body 110, causing the tip 140 to rotate substantially in unison with the handle 130. In some embodiments, the handle 130 is made of polymer. In at least one embodiment, the handle 130 is made of polycarbonate.

Figure 2A:
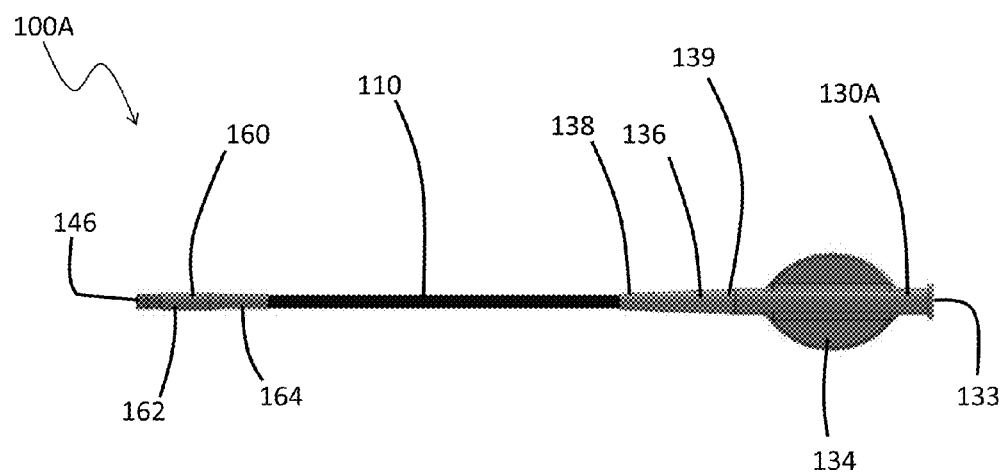
FIG. 2A is a plan view of a second embodiment of a device for providing access across an occlusion for therapy devices.
Figure 3:
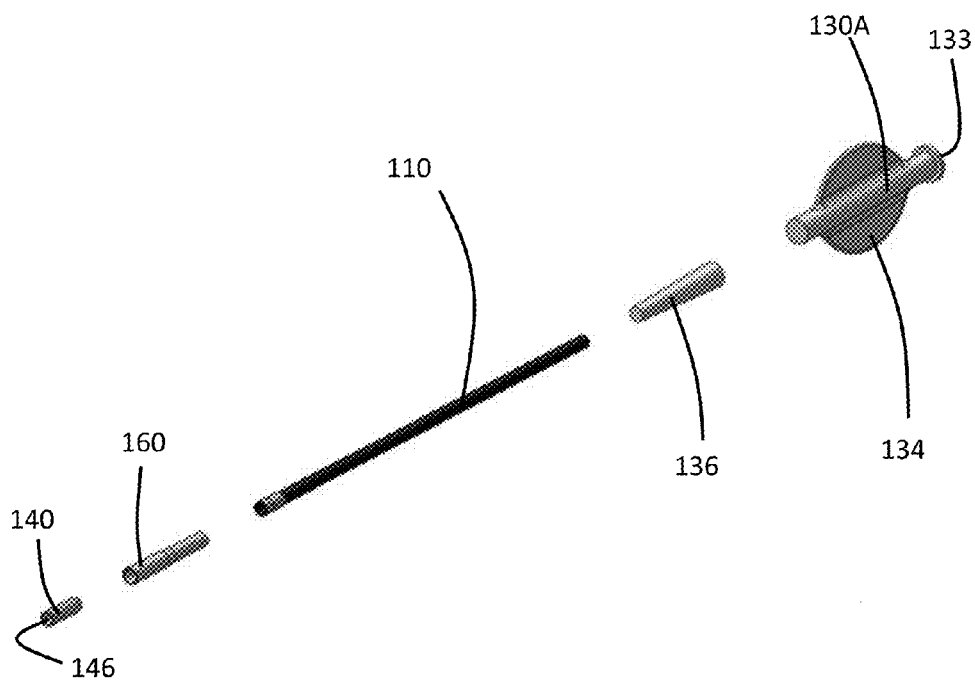
FIG. 3 is an exploded perspective view of the second embodiment of a device of FIG. 2A.

FIG. 2A depicts an embodiment of a clearing device 100A that is similar to the clearing device 100 except as set forth differently below. The clearing device 100A can be used with one or more components of the system 50. In this embodiment, a handle 130A is provided that includes at least one rib 134 that enhances a user's ability to apply torque by finger pressure to the elongate body 110. In the illustrate embodiment, the handle 130A has two ribs that are disposed on opposite sides of the body of the handle 130A. This structure enables a user to apply pressure by a thumb and index finger of a single hand to rotate the clearing device 100A. This provides for easy abrading or cutting action, with the procedure being performed with just one or two hands. For instance, as discussed more below, this approach enables a user to hold a guidewire in one hand and the clearing device 100A in the other hand and to provide rotation of the clearing device over the guidewire when so held.

In another technique, by altering the tension or compression on the guidewire the user can direct the leading edge of the clearing device 100, 100A. If the wire bows under compression, for example, the trajectory of the clearing device 100 can be altered. A plurality of wires of different bending stiffness could be used to vary the bending stiffness under compression. In one case, two or three wires are provided which will be relatively stiff and could clear cause some enlargement of the occluded lumen. If operation of the clearing device 100 is to commence, one or more of the wires can be removed. For instance a first wire can be removed so that the remaining wires will bow under compression. A tangent to the bent wire(s) that remain will define the trajectory of the clearing device 100, 100A. In a further step, all wires can be removed to permit the clearing device 100, 100A to be advanced without support, and unguided from that point on. For progressive enlargement a series of clearing devices 100 could be used to enlarge the lumen slightly more for each device.

In some embodiments, the handle 130A is joined to the elongate body 110, which is of a different configuration, e.g., a different material or physical structure. In such arrangements, a strain relief structure can be provided between the handle 130A and the elongate body 110 to minimize kinking or other failure modes. One example of a strain relief structure includes a collar 136 that couples handle 130A to the elongate body 110. In at least one embodiment, the collar 136 is bonded to the handle 130A using an adhesive. In some embodiments, the collar 136 is tapered such that a distal end 138 of the collar 136 has an outer diameter that is smaller than the outer diameter of a proximal end 139 of the collar 136. In several embodiments, the collar 136 is made of polymer. In at least one embodiment, the collar 136 is made of nylon. In at least one embodiment, the collar 136 is made of polyether block amide (PEBA). Other functions of the strain relief include one or more of the minimization of kinking during general handling, tracking and torqueing of the catheter, facilitating the bonding of a larger diameter handle to the smaller diameter catheter body, providing a surface for the printing of catheter specifications or color to denote the configuration of the catheter.

In several embodiments, the clearing device 100 comprises a sleeve 160 that surrounds at least a portion of the elongate body 110. In some embodiments, the sleeve 160 strengthens the junction of the tip 140 to the elongate body 110. In several embodiments, the sleeve 160 minimizes abrupt diameter changes that may result during assembly of the tip 140 to the elongate body 110. In some embodiments, the sleeve 160 surrounds the distal portion of the elongate body 110. In at least one embodiment, the sleeve 160 surrounds the proximal portion of the tip 140 and the distal portion of the elongate body 110. In some embodiments, a distal portion 162 of the sleeve 160 has an outer diameter that is larger than the outer diameter of a proximal portion 164 of the sleeve 160. In at least one embodiment, the sleeve 160 is made of shrink tubing material. Other functions of or modes of operation of the sleeve 160 (e.g., shrink tubing 160) include providing any or all of the following:

lubricity—the outer surface may be made of a material that is more slippery or made to be more slippery than the catheter body thus facilitating tracking and torqueing the catheter;

support—the sleeve may be configured to increase the longitudinal stiffness of the distal portion of the catheter, resulting in the cutting tip being guided in a straight; and/or protection—the sleeve covers the trailing edge of the cutting tip and protects it from being dislodged during tracking and torqueing.

Although illustrated as a separate layer that is applied to the elongate body 110, the sleeve 160 could be configured as a coating or could include a coating disposed over it.

Figure 4:
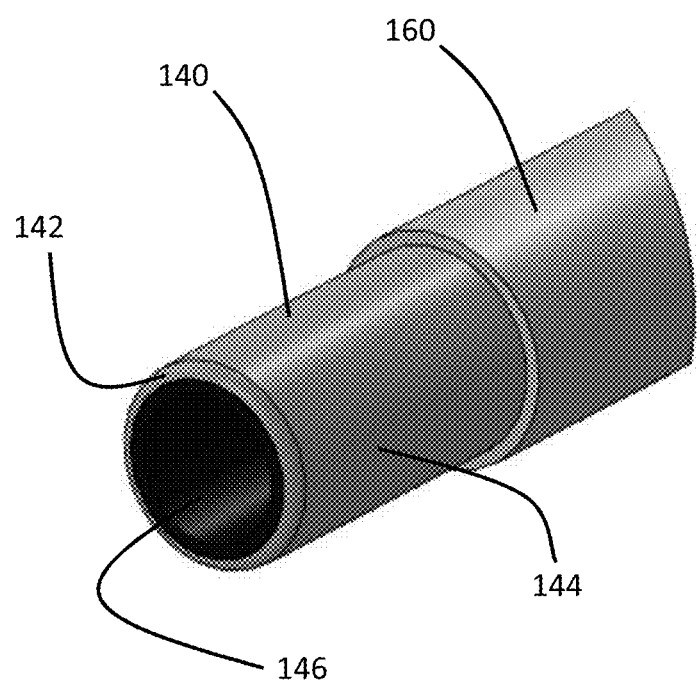
FIG. 4 is a perspective detail view of a distal portion of one variation of an occlusion crossing device, which can be incorporated into various embodiments including the first or second embodiments.
Figure 5:
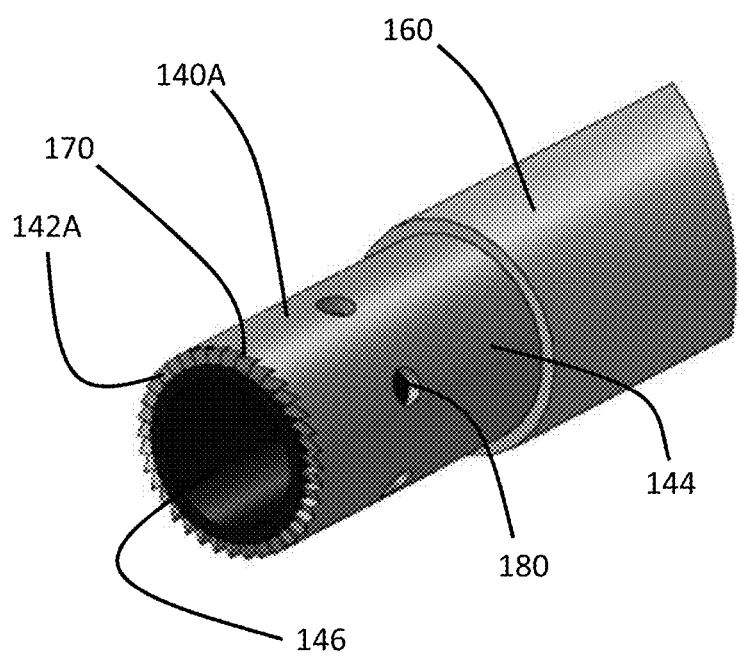
FIG. 5 is a perspective detail view of a distal portion of another variation of an occlusion crossing device, which can be incorporated into various embodiments including the first or second embodiments.

FIGS. 4 and 5 depict illustrative embodiments of the tip 140. As discussed below, the tip 140 interacts with the lesion tissue and is configured to remove or displace lesion tissue. In several embodiments, the tip 140 is configured to remove lesion tissue through different modes of operation including cutting, tearing, shaving, or abrading the lesion tissue. The tip 140 may be configured to use one, or more than one, method of removing lesion tissue. In several embodiments, the tip 140 provides lateral support to the guidewire as the guidewire is advanced through a stenosis. In some embodiments, the tip 140 can prevent the guidewire from buckling as the guidewire is advanced through an occlusion or a near total occlusion. In providing this function, the tip 140 can be configured with a bore having a diameter that is close to that of the guidewire, e.g., within about 10% of the diameter of the guidewire. The gap between the guidewire and the clearing device 100 should be large enough to keep resistance to relative movement (advancement and/or rotation) between these components to an acceptable level for tracking and twisting. In addition, the clearing device 100 may be used as an exchange device for changing guidewires or other interventional devices without losing position or access to the target lesion. The lumen in the clearing device 100 can be used for drug delivery and contrast injection as needed.

The tip 140 has a distal face 142, a side surface 144, and a distal opening 146. In the embodiment of the tip 140 shown in FIG. 4, the distal face 142 of the tip 140 is disposed generally at a plane extending transverse to the longitudinal axis of the tip 140. The face 142 can also be beveled, such that it is rounded in a proximal direction from such a plane, e.g., toward and outer surface of the tip 140. This arrangement is advantageous in that a longitudinal force along the axis of the clearing device 100 will produce a generally straight trajectory of the tip 140 as it advances. The distal face 142 can be disposed on a plane at an acute angle to the longitudinal axis in certain embodiments, but disposing the distal face 142 on a transverse plane results in less deflection of the tip upon advancement or rotation.

In some embodiments the tip 140 can be beveled and serrated. An example of a serrated tip provides a plurality of sharp edges on the surface 140 disposed around the circumference of the tip 140. The sharp edges can be elongated and disposed on the side surface 144. The edges can be axial edges. The edges can be spiral edges. In some embodiments, the sharp edges can be configured for removing material from the clearing zone disposed around the distal face 142. In some embodiments, teeth or other cutting structures can be disposed on the inside of the lumen extending proximally from the distal opening 146. Cutting structures disposed on the side surface 144 can have an arcuate configuration facing the direction of the cut. For example, the cutting surface can have an angle of attack facing the direction of motion of the clearing device. The cutting surface can be position to maximally cut upon rotation of the clearing device 100 in some embodiments. The cutting surface can be positioned to maximally cut upon advancement of the clearing device 100 in some embodiments. In some embodiments, the distal face 142 is blunt (not shown). In at least one embodiment, the distal face 142 is abrasive. In the embodiment of the tip 140A shown in FIG. 5, the distal face 142A has a plurality of cutting teeth 170. The face 142A can also be considered to be disposed on a transverse plane, for example if the distal aspects or proximal aspects of the teeth 170 are disposed at the same plane disposed transverse to the axis of the tip 140A. In some embodiments, the cutting teeth 170 are configured to hold the lesion tissue fixed relative to the tip 140A, allowing the clearing device 100 to tear lesion tissue away from vessel wall. In some embodiments, the cutting teeth 170 are configured to slice through the lesion tissue, allowing the clearing device 100 to remove lesion tissue in a manner that minimizes twisting stress on the vessel wall.

In several embodiments, the side surface 144 of tip 140 includes an element for moving displaced or separated abraded matter from the working zone of the clearing device 100. For example, in one embodiment at least one flute 180 serves to debulk the lesion as the tip 140 rotates within the stenosis 20. In some techniques, aspiration is provided through a main (e.g., central) lumen of the clearing device 100. In some approaches, if a guidewire is present, aspiration through the main lumen can be enhanced by removing the guidewire.

In some embodiments, the flute 180 includes a hole that passes through the tip 140. In at least one embodiment, the flute 180 communicates with a lumen, e.g., a dedicated aspiration lumen (not shown) or the central lumen 114 of the elongate body 110. If the abraded matter is to be aspirated out of the clearing device 100, 100A or otherwise segregated therein, a dedicated lumen may be preferred in that the sliding contact between the inner surface 116 of the elongate body 110 and the outer surface of the guidewire should remain as debris-free as possible to reduce the chance of these surfaces becoming seized. In other embodiments, a greater gap is provided between the inside surface of the elongate body 110 and a guidewire positioned therein and abraded or separated matter from the occlusion can be aspirated or sequestered in the main lumen. In at least one embodiment, the flute 180 is a circular hole having a diameter of 6.6 mm.

Other uses for the flutes 180 are to confirm the status of the clearing device 100. For example, an imaging agent can be delivered through a lumen in fluid communication with the flutes. The pattern of the images indicates the status of the clearing device. In one instance, the imaging agent may not emerge from the clearing device 100. The clinician can then know that the clearing device 100 is occluded and could be removed and either cleared or replaced with a second clearing device. In another instance, the imaging agent can indicate whether the occlusion of the vessel is sufficiently enlarged for other treatment. In another instance, the imaging agent may indicate that a different mode of use of the clearing device 100 should be used. For example, if one side of the clearing device 100 is occluded a second side of the device could be rotated into position to further clear the lumen.

Figure 5A:
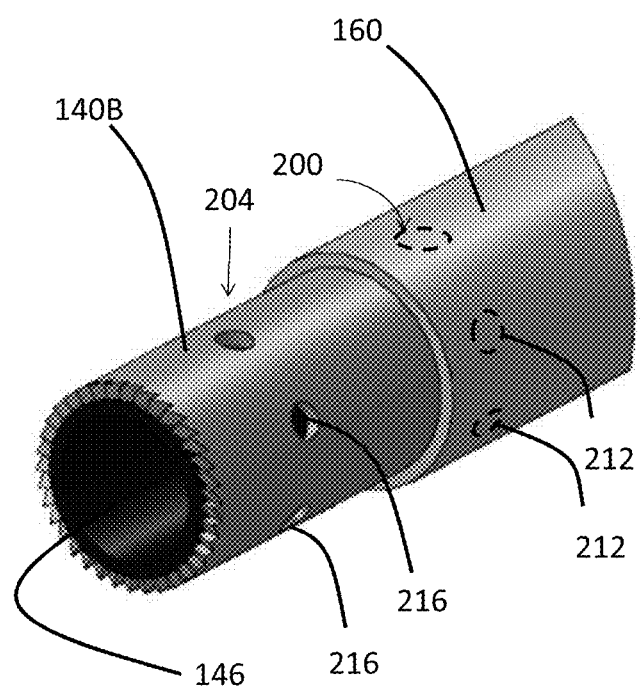
FIG. 5A is a perspective detail view of a distal portion of another variation of an occlusion crossing device, which can be incorporated into various embodiments including the first or second embodiments.

In some embodiments, apertures similar to the flutes 180 can be provided through the tip 140A to provide for securement to other parts of the clearing device. For example, the tip 140A can be configured as a metal cylinder to be joined to an elongate polymeric catheter body. To secure the cylinder, holes in the cylinder can be configured and positioned to have portions of the catheter flow or extend into the holes. In one technique a polymeric body of the clearing device 100 disposed on the inside of the cylinder is formed such that a portion thereof protrudes radially outwardly into the holes. In one technique a polymeric body of the clearing device 100 disposed on the outside of the cylinder is formed such that a portion thereof protrudes radially inwardly into the holes. FIG. 5A shows an example where holes are disposed beneath the sleeve 160. The sleeve is applied to a portion of the side surface 144 of the tip 140A such that the sleeve extends into the holes. This provides for securement of the cylinder to prevent it from slipping off the elongate body 110 or from being displaced proximally which would interfere with the clearing function.

The elongate body 110 proximal of the tip 140 must be flexible to enable the clearing device 100 to travel through a tortuous vasculature for certain applications, e.g., for coronary or neurovascular procedures. At the same time, the elongate body 110 must be stiff to transmit compressive and torsional forces to the tip 140. In several embodiments, the elongate body 110 is made of polymer. In some embodiments, the elongate body 110 is made of a polymeric material selected from the group consisting of polyimide, and PEBA. In some embodiments, the elongate body 110 is made of one material embedded in another material. In an embodiment depicted in FIG. 6, the elongate body 110 is made of a mesh material 190 embedded in a coat material 194. In at least one embodiment, the mesh material 190 includes 304-stainless steel flat wire braid. In at least one embodiment, the coat material 194 is made of a polymer, such as polyimide and/or PEBA. In some embodiments, multiple layer and multiple polymers may be employed. In addition, in several embodiments the elongate body can be fashioned from a material or composite structure at the proximal end to provide more push such as a hypotube and be attached to a material of softer stiffness to facilitate tracking and delivery of the cutting tip.

In several embodiments, the clearing device 100 is used in conjunction with a guidewire (not shown). In many embodiments, a guidewire is advanced endovascularly until the distal end of the guidewire reaches a stenosis targeted for angioplasty. In some embodiments, the clearing device 100 is mounted onto a guidewire by feeding the proximal end of the guidewire into the distal opening 146 of the tip 140. The guidewire is then passed through the central lumen 114 of the capture device 110, and drawn out of the proximal opening 133 of the handle 130. The tip 140 is advanced along the guidewire until the distal face 142 of the tip 140 encounters the lesion 17. As discussed elsewhere herein, close clearance between the lumen 114 and a guidewire help to reduce the crossing profile. In some embodiments and in some techniques, having close clearing also helps in bracing the guidewire. Bracing is not required for various embodiments and techniques. In some cases, a guidewire is not needed in any aspect of the method.

In some embodiments, the tip 140 is used to gently abrade the lesion 17. Once the distal face 142 makes contact with the lesion 17, a user applies torque to the handle 130, causing the handle 130 to rotate about the guidewire. The elongate body 110 transmits the torque to the tip 140, causing the distal face 142 of the tip 140 to slide over the surface of the lesion 17. In many embodiments, a user rotates the handle 130 in alternating clockwise and counterclockwise directions. In some embodiments, the handle 130 is rotated in only one direction. In some embodiments, a user applies compressive forces by pushing the handle 130 in the distal direction. In some embodiments, a user applies simultaneously compressive and torsional forces by pushing the handle 130 in the distal direction while rotating handle 130 about the guidewire.

In several embodiments, the tip 140 is configured to resist deformation. In some embodiments, the tip 140 is made of an alloy possessing high strength properties. In at least one embodiment, the tip 140 is made of seamless drawn tubing of L-605 composition. In several embodiments, the tip 140 defines a circular lumen. In at least one embodiment, the tip 140 has an inner diameter of 1.25 mm and a circularity of less than 0.0050 mm. In at least one embodiment, the tip 140 is a hollow cylinder with an outer diameter of 1.45 mm, a wall thickness of 0.2 mm, and a length of 4.5 mm. As noted above, configuring the tip to avoid being deformed out of round provides assurance that the clearing device 100, 100A will not seize up upon the guidewire, preventing relative rotation. In at least some embodiments, a close fit between the guidewire and the clearing device 100, 100A is provided so that the clearing device 100 can provide a bracing effect to the guidewire. This bracing effect enables the guidewire to be advanced distally out of the abrading device in a mode of operation where the guidewire is urged forward across the lesion. In order to provide this bracing effect while still maintaining the clearing device 100 rotatable over the guidewire, out of round of the inner diameter should be reduced, minimize or eliminated.

FIG. 5A illustrates another tip arrangement that can be provided on any of the clearing or cutting devices disclosed herein. The embodiment includes a tip 140B that includes a first structure 200 for providing a mechanical interface between the tip 140B and an elongate catheter assembly and a second structure 204 for removing or retaining matter removed from the lesion 17 during the procedure. The first structure 200 can include one or a plurality of recesses 212. The recesses 212 form a part of an interface disposed between the tissue modifying surface, which can include a ring or ring structure of the tip 140B and one or both of the sleeve 160 and the elongate body 110, which can be disposed within the tip 140B. The recesses 212 can be formed around a circumference of the tip 140B, e.g., at equal angular spaced apart circumferential locations. The recesses 212 can be holes disposed entirely through the ring structure of the tip 140B. The sleeve 160 and/or the elongate body 110 can interface with the tip 140B by protruding into the recess 212. In other embodiments, the recesses 212 can disposed on an inside surface of the sleeve 160 or an outside surface of the elongate body 110 and a lateral protrusion formed on the tip 140B can protrude into the recesses. The interface between the recesses 212 and the elongate catheter assembly can be disposed at least partially in a radial direction. As such, an axial load can be transmitted across the interface such that a pushing, pulling or rotational force is directly transmitted from the proximal end to the tip 140B. Also, the interface formed in and by the recesses 212 provide supplemental securement to the tip 140B such that it will not detach from the elongate body 110.

The second structure 204 can include a plurality of apertures 216 disposed about the circumference of the tip 140B. The holes provide for the tip 140B to take in matter that is liberated from the lesion 17. As discussed above, the aperture 216 can be blind end holes or can extend entirely through the tip 140B and be in fluid communication with a lumen for aspiration or retention of the matter. The second structure 204 can be arranged at one axial position or can be an array of holes disposed along a length of the tip 140B.

The second structure 204 can be in communication with a source of fluid, e.g., through the branch 90, such that fluid can be injected through an aperture or through an array of apertures. The fluid can be a medication or can act as a lubricant to facilitate motion. The fluid can be a contrast medium such that the outflow through the apertures of the second structure 204 can indicate the degree of fill of the interior of the clearing device 100.

In various embodiments, the second structure 204 can include apertures of different types such that distal-most apertures may extend partly through the wall of the tip portion 140B while apertures proximal thereof may extend entirely through the wall to provide fluid communication between an outside of the clearing device 100 and a lumen therein. That way more distal apertures can fill without obstructing the lumen. Once the distal-most apertures are filled, the more proximal holes will become obstructed and prevent contrast from flowing out of the device 100 indicating the device is full or nearly full.

A further embodiment is illustrated in connection with FIG. 6. In particular, a tip (such as the tip 140, 140A, 140B) can be attached to the mesh 190 at the distal end of the mesh 190. The distal end of the tip can be disposed proximally of the distal end of the lining 120 or proximal to the distal end of the distal-most section of the coat material 194. For example, the distal end of the tip can be at the line L in FIG. 6. This provides a bumper zone 220 distal to the end of the tip 140, 140A, 140B. The bumper zone 220 can prevent an unintentional interaction with an un-diseased vessel wall. The bumper zone 220 is generally more deformable than the tip 140, 140A, 140B so under a higher force it will either compress axially or radially under the lesion 17 thus not preventing the treatments discussed above.

Figure 5B:
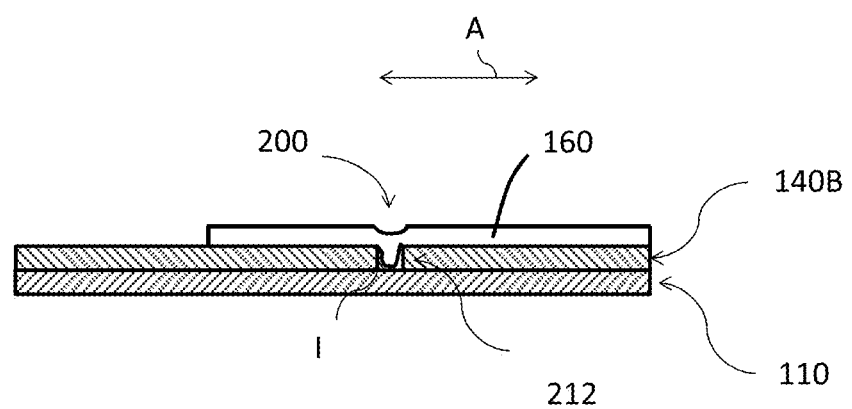
FIG. 5B schematically shows one embodiment of a mechanical interface between a tip portion and a catheter assembly.

FIG. 5B shows a partial cross-section of one wall of a catheter device 100, 100A around the structure 200 for providing a mechanical interface. An interface is disposed between the ring structure of the tip 140B and the elongate catheter assembly. The interface I provides a protrusion of the layer 160 into the recesses 212 as shown. In alternative embodiment, the layer 110 can extend radially outwardly into the recess 212. The interface is at least partially in a radial direction in that a portion of the layer 160 is deformed into recess 212. An axial load can be transmitted across the interface I in the direction of the arrow A. In some embodiments, the interface is provided such that a protrusion and recess overlap in the axial direction. The distal aspect of the aperture 212 can be just distal of (axially in front of) a portion of the layer 160. The proximal aspect of the aperture 212 can be just proximal of (axially behind a portion of the layer 160.

In some embodiments, radial stiffness and resistance to deformation should be minimal at least in an occlusion clearing portion. A braid, such as the mesh material 190, can be used to reduce or eliminate deformation of the inner diameter.

In at least one embodiment the tip has an oval or non-round outer profile or is disposed radially or laterally away from an axis of rotation of the catheter assembly. Such an arrangement provides that when the clearing device is rotated about the guidewire it creates a circular lumen larger with a cross-sectional area greater than the cross-sectional area of the crossing device. In one embodiment, an oval or other non-round outer profile may be best for softer material. Round outer profile may be better to provide a more focused force to clear harder materials.

Another advantage of a structure maintaining inner diameter stability is that crossing profile and clearance will be more constant and more predictable. In contrast, if the tip compresses and the tip deforms, the profile of the tip may be reduced, which will reduce the effectiveness in clearing the lumen. If the inner diameter is collapsed, the clearance may be reduced or eliminated. Reducing or eliminating clearance may result in cutting off the ability to remove severed matter form the clearing device 100. This may result in blockage of the device and the need to replace the clearing device 100.

ADDITIONAL METHODS

Figure 7A:
FIG. 7A illustrates under fluoroscopic imaging a patient having a chronic total occlusion, which patient is in dire need for a device that can quickly and safely cross the chronic total occlusion.
Figure 7B:
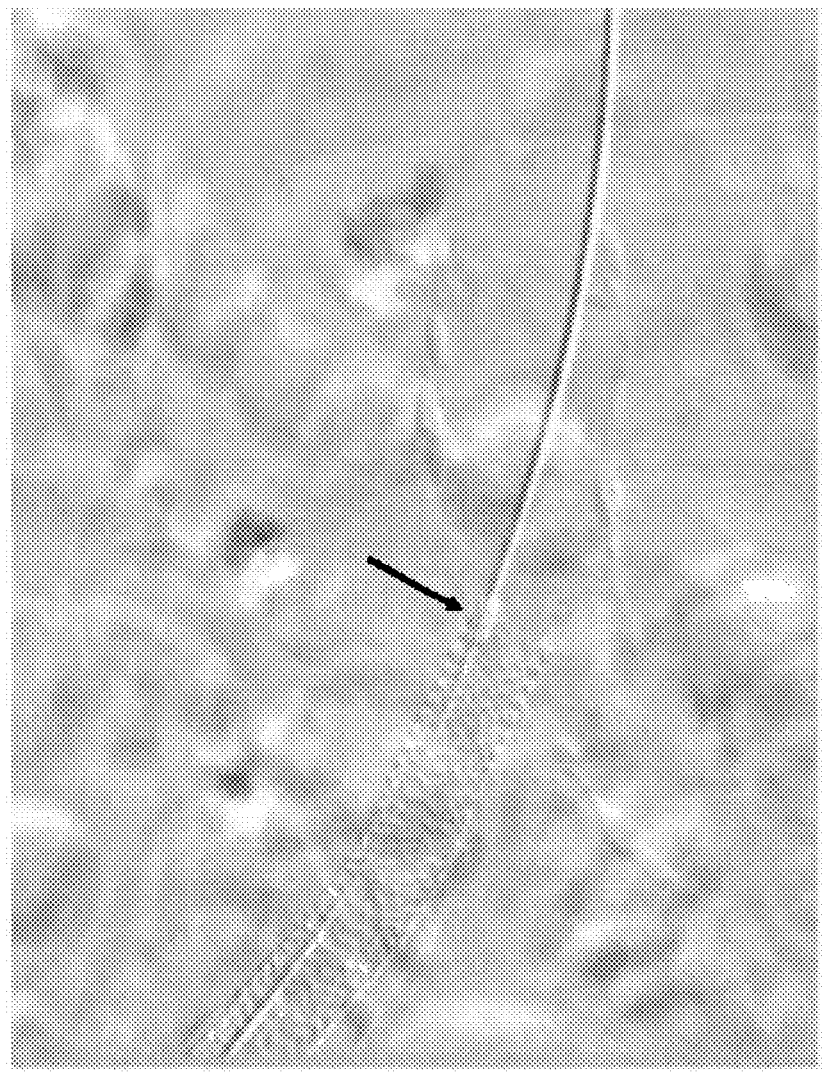
FIG. 7B illustrates under fluoroscopic imaging a system including a guidewire and an anchorable and/or rotatable crossing device advanced through a patient portion of an artery, toward a total occlusion.
Figure 7C:
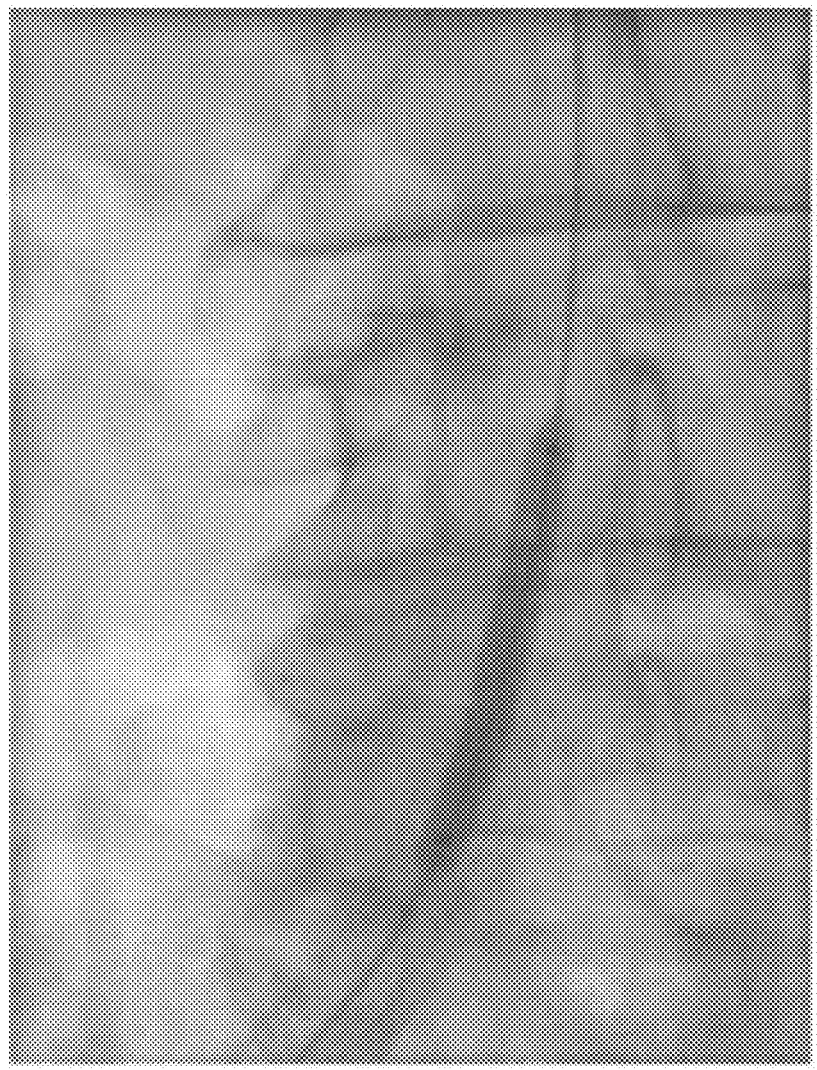
FIG. 7C illustrates under fluoroscopic imaging a treatment device being position over the guidewire of the system of FIG. 7B through the total occlusion.
Figure 7D:
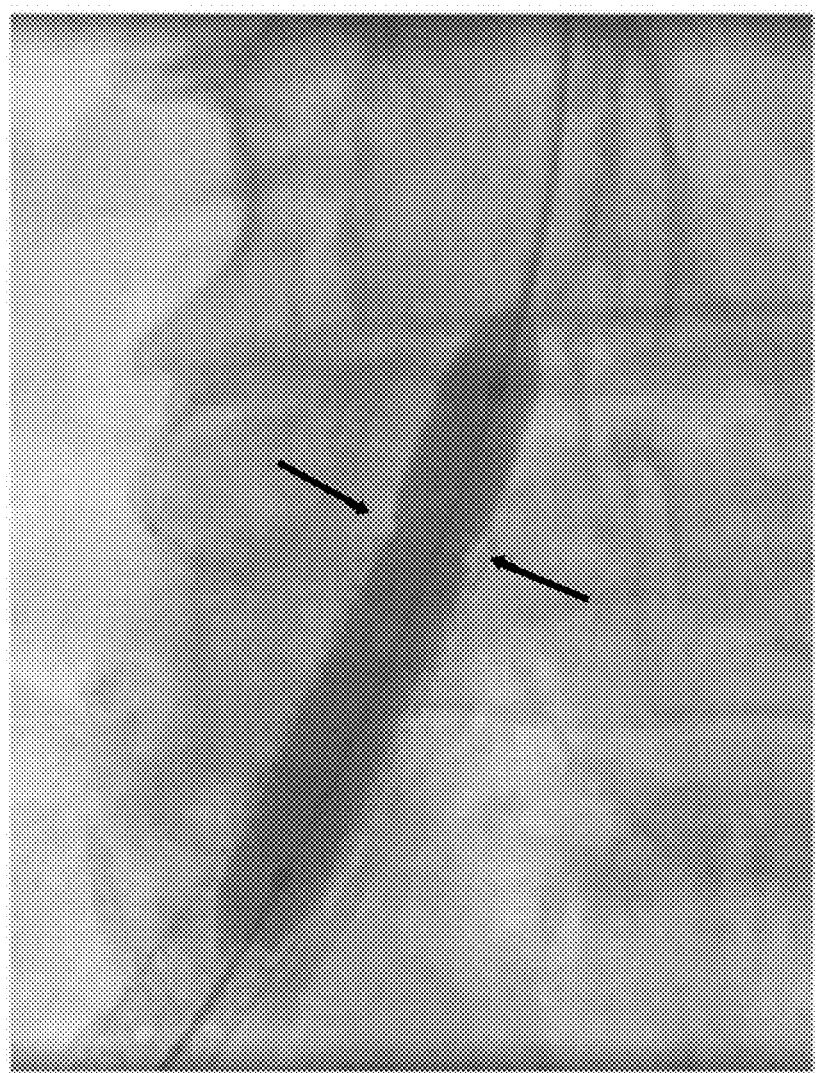
FIG. 7D illustrates under fluoroscopic imaging advancement of the treatment device entirely through the total occlusion to facilitate expansion of a balloon catheter.
Figure 7E:
FIG. 7E illustrates the same vessel segment of illustrated in FIG. 7A, where the occlusion has been opened and the flow restored.

An actual use of a clearing device similar to the clearing device 100 and the system 50 is illustrated by FIGS. 7A-7F. FIG. 7A illustrates under fluoroscopic imaging a patient having a chronic total occlusion. The dark region shows that contrast media that has been injected is trapped upstream of the occlusion. FIG. 7B illustrates the device under fluoroscopic imaging a system. The clearing device 100 is disposed over a guidewire. The clearing device is positioned to be (and is after the point in time recorded in FIG. 7B) advanced through the occlusion. FIG. 7C illustrates under fluoroscopic imaging a balloon catheter disposed over the guidewire and across the occlusion. FIG. 7D illustrates under fluoroscopic imaging the balloon expanded at and on both sides of the occlusion. The arrows point to a narrowing of the balloon at the site of the occlusion showing that the remains of the occlusion are more rigid than the balloon. FIG. 7E illustrates the same vessel segment of illustrated in FIG. 7A, where the occlusion has been opened and the flow restored.

EXAMPLES

Example 1

Treatment of In-Stent Restenosis

A 54-year-old male presented Stage IIb peripheral artery disease (PAD) arising from restenosis of a stent placed in the right common iliac artery four years earlier. A 0.035-inch diameter PTFE endovascular guidewire was inserted into the patient and advanced across the region of stenosis. A balloon catheter was then mounted onto the guidewire in an over-the-wire (OTW) configuration and advanced to the region of stenosis. The balloon catheter was unable to cross the target stenosis. The balloon catheter was withdrawn from the patient, and an embodiment of the clearing device 100 was mounted onto the guidewire in an OTW configuration. In this and the following examples, embodiments of the clearing device 100 were used. The embodiment of the clearing device 100 used to treat this patient had a 0.035 inch inner diameter and a leading edge outer diameter of 0.071 inch. As discussed above, the serrated tip was used to advance the catheter in resistance lesions by abrading or cutting through the inner luminal edges of the vessel stenosis in much the same way that a saw is used to cut through a piece of wood. While the blunt or beveled tip is used more like a shoe horn but also may have to some degree abrading abilities.

The embodiment of the tip 140 used to treat this patient had a distal surface 142 that was blunt and abrasive. The clearing device 100 was advanced along the guidewire until the distal surface 142 of the tip 140 made contact with the lesion tissue. The distal surface 142 of the tip 140 gently abraded the lesion tissue. Gentle abrasion was achieved by pushing the handle 130 in the distal direction and, at the same time, rotating the handle 130 about the guidewire. The handle 130 was rotated in both directions during the abrading procedure.

As the lesion tissue was abraded, the clearing device 100 was advanced along the guidewire until the tip 140 had crossed the region of stenosis. After the tip 140 had crossed the region of stenosis, the clearing device 100 was withdrawn from the patient, and a balloon catheter was remounted on the guidewire in an OTW configuration. The balloon catheter was advanced along the guidewire to reach the target stenosis. The balloon catheter was now able to enter the region of stenosis because the clearing device 100 had abraded the target lesion and enlarged the stenosis, allowing the stenosis to accommodate the profile of the balloon catheter. Once the balloon catheter was positioned within the lumen of the target stenosis, the balloon was inflated to further enlarge the stenosis. After balloon angioplasty, the balloon catheter was removed from the patient. Radiography confirmed blood flow was restored in the targeted vessel.

Example 2

Recanalization of the Superficial Femoral Artery

A 70-year-old male presented Stage IIb peripheral artery disease (PAD) arising from occlusion of the superficial femoral artery. Radiographic imaging indicated the occlusion affected a length of >25 cm of artery, with the patient having 95% truncus tibiofibularis stenosis. A 0.035-inch diameter endovascular guidewire was inserted into the patient and advanced across the region of stenosis. A balloon catheter was mounted onto the guidewire in an over-the-wire (OTW) configuration and advanced to the region of stenosis. The balloon catheter was unable to cross the target stenosis. The balloon catheter was withdrawn from the patient, and an embodiment of the clearing device 100 was mounted onto the guidewire in an OTW configuration. The embodiment of the clearing device 100 used to treat this patient had a 0.035 inch inner diameter and a leading edge outer diameter of 0.071 inch.

The clearing device 100 was advanced along the guidewire until the distal surface 142 of the tip 140 made contact with the lesion tissue. The distal surface 142 of the tip 140 gently abraded the lesion tissue. Gentle abrasion was achieved by pushing the handle 130 in the distal direction and, at the same time, rotating the handle 130 about the guidewire. The handle 130 was rotated in both directions during the abrading procedure. Applying gentle pressure on the handle 130 ensured the distal surface 142 of the tip 140 was abrading the lesion by moving over the lesion surface. If pressure is applied too strongly to the handle 130 the lesion tissue may merely twist in unison with the distal surface 142 of the tip 140, making the abrading procedure ineffective. As the lesion tissue was abraded, the clearing device 100 was advanced along the guidewire until the tip 140 had crossed the region of stenosis. After the tip 140 had crossed the region of stenosis, the clearing device 100 was withdrawn from the patient and angioplasty was performed. Radiography confirmed blood flow was restored in the treated vessel.

Example 3

Treatment of Short Superficial Femoral Artery Occlusion

An 86-year-old male presented Stage IIb peripheral artery disease (PAD) arising from occlusion of the superficial femoral artery. Radiographic imaging indicated the occlusion affected a length of <6 cm of artery. A 0.035-inch diameter endovascular guidewire was inserted into the patient and advanced across region of stenosis. A balloon catheter was mounted onto the guidewire in an over-the-wire (OTW) configuration and advanced to the region of stenosis. The balloon catheter was unable to cross the target stenosis. The balloon catheter was withdrawn from the patient, and an embodiment of the clearing device 100 was mounted onto the guidewire in an OTW configuration. The embodiment of the clearing device 100 used to treat this patient had a 0.035 inch inner diameter and a leading edge outer diameter of 0.071 inch.

The tip 140 of the clearing device 100 was moved to the target lesion by advancing the handle 130 distally along the guidewire. Once the distal face 142 of the tip 140 was in contact with the target lesion, the handle 130 of the clearing device 100 was gently pushed in the distal direction and rotated back-and-forth about the guidewire, causing the distal face 142 to gently abrade the target lesion. This method of lesion abrasion was continued until the tip 140 of the clearing device 100 had crossed the region of stenosis. Once the tip 140 crossed the lesion, the clearing device 100 was withdrawn from the patient by pulling the handle 130 in a proximal direction until the clearing device 100 was removed from the guidewire. Next, a balloon catheter was mounted onto the guidewire for use in balloon angioplasty. The balloon catheter was mounted on the guidewire in an OTW configuration and advanced along the guidewire to reach the target stenosis. The balloon catheter was now able to enter the region of stenosis because the clearing device 100 had abraded the target lesion and enlarged the stenosis, allowing the stenosis to accommodate the profile of the balloon catheter. Once the balloon catheter was positioned within the lumen of the target stenosis, the balloon was inflated to further enlarge the stenosis.

After balloon angioplasty, the balloon catheter was removed from the patient, and a delivery catheter carrying an expandable stent was mounted onto the guidewire in an OTW configuration. The delivery catheter was advanced along the guidewire until the DES was within the lumen of the target stenosis. The stent was then deployed to maintain the enlarged lumen and restore blood flow to the previously occluded vessel.

Example 4

Treatment of Truncus Tibiofibiolaris Stenosis

A 72-year-old male presented Stage IV peripheral artery disease (PAD) arising from calcified below-the-knee (BTK) 99% truncus tibiofibiolaris stenosis. After a successful wire-crossing of the stenosis by a 0.014-inch diameter guidewire, a 1.2 mm outer diameter over-the-wire balloon catheter was advanced along the guidewire using a 1.5 mm diameter push catheter. The balloon catheter was unable to cross the stenosis. The balloon catheter was withdrawn from the patient and an embodiment of the clearing device 100 was mounted onto the guidewire in an OTW configuration. The embodiment of the tip 140 used for this example had a 0.018 inch inner diameter and a leading edge outer diameter of 0.063. The handle 130 was moved distally along the guidewire to advance the tip 140 to the target lesion. Once the distal face 142 of the tip 140 was in contact with the target lesion, the handle 130 of the clearing device 100 was gently pushed in the distal direction and rotated back-and-forth about the guidewire to cause the distal face 142 to gently abrade the target lesion.

This method of lesion abrasion was continued until the tip 140 of the clearing device 100 had crossed completely the region of stenosis. Once the tip 140 crossed the lesion, the clearing device 100 was withdrawn from the patient by pulling the handle 130 in a proximal direction until the clearing device 100 was removed from the guidewire. Next, a blade angioplasty catheter was again mounted onto the guide wire in an OTW configuration. The blade angioplasty catheter was advanced along the guidewire. The blade angioplasty catheter was now able to enter the region of stenosis because the clearing device 100 had abraded the target lesion and enlarged the stenosis, allowing the stenosis to accommodate the profile of the blade angioplasty catheter. The blade angioplasty catheter was used to further enlarge the stenosis. After blade angioplasty, the blade angioplasty catheter was removed from the patient, and a delivery catheter carrying an expandable drug-eluting stent (DES) was mounted onto the guidewire in an OTW configuration. The delivery catheter was advanced along the guidewire until the DES was within the lumen of the target lesion. The DES was then deployed to maintain the enlarged lumen and restore blood flow to the previously occluded vessel.

The above presents a description of modes contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A support catheter for an occlusion crossing procedure, comprising:
    an elongate body extending between a proximal end and a distal end, the elongate body having a lumen for receiving and supporting a guidewire;
    a crossing tip disposed on a distal portion of the support catheter, the crossing tip having a ring structure with an inner surface that is radially outward of and fixedly attached to an outside surface of the elongate body, the crossing tip being configured to be advanced and/or rotated in a reciprocating motion to actively remove material forming the occlusion upon advancement and/or rotation; and
    a flexible bumper zone distal to the crossing tip, the flexible bumper zone being immobilized relative to and extending distally of the crossing tip, the flexible bumper zone coupled with one or both of the elongate body and the inner surface of the ring structure and extending distally beyond the distal end of the ring structure.

2. The catheter device of claim 1 further comprising:
    a sleeve having an inside surface disposed radially outward of an outside surface of the crossing tip and fixedly attached to a proximal portion of the tip such that there is no relative motion between the sleeve and the crossing tip.

3. The catheter device of claim 1, wherein the crossing tip comprises a cutting blade.

4. The catheter device of claim 1, wherein the crossing tip comprises an abrasive surface.

5. The catheter device of claim 1, wherein the crossing tip comprises a side surface with at least one opening extending inwardly from the side surface.

6. The catheter device of claim 5, wherein the side surface comprises at least one channel in fluid communication with an aspiration lumen.

7. The catheter device of claim 1, wherein the lumen of the elongate body has an inner diameter of approximately 0.020 inch to 1.00 inch.

8. The catheter device of claim 1, wherein the crossing tip has a length and a width, the length being more than two times the width thereof.

9. The catheter of claim 1, further comprising at least one recess disposed on an outer surface of the crossing tip, the at least one recess configured to accommodate material dislodged from a lesion at the occlusion.

10. The catheter of claim 9, wherein the at least one recess comprise a plurality of openings formed through the cylindrical body.

11. The support catheter of claim 1, wherein the elongate body is configured to provide a 1:1 transmission of torque between the proximal end and the distal end.

12. The support catheter of claim 1, wherein the crossing tip comprises a hoop strength of 15 psi.

13. The support catheter of claim 1, wherein the crossing tip retains a minimum diameter of about 90% of its initial diameter upon application of a crush force of about 3 Newtons.

14. The support catheter of claim 1, further comprising an interface and at least one opening extending inwardly from a side surface of the crossing tip and a radial projection extending into the at least one opening such that the projection is axially overlapping with at least a portion of the at least one opening.

15. The support catheter of claim 1, further comprising an interface that comprises a sleeve having a proximal portion coupled with the outside surface of the elongate body and a distal portion disposed in a recess disposed on an outside surface of the crossing tip.

16. The support catheter of claim 1, wherein an inner periphery of the crossing tip is configured to retain its shape upon acting on the occlusion so as not to impede the reciprocating motion.

17. The support catheter of claim 1, wherein the bumper zone is more deformable than the crossing tip.

18. The support catheter of claim 1, wherein the outside surface of the elongate body is an exterior surface of the support catheter such that the outside surface of the elongate body is exposed when the support catheter is advanced within the vasculature.

* * * * *